(12) United States Patent
Jackson et al.

(10) Patent No.: US 8,460,190 B2
(45) Date of Patent: Jun. 11, 2013

(54) AUTOMATED IMAGE INTERPRETATION WITH TRANSDUCER POSITION OR ORIENTATION SENSING FOR MEDICAL ULTRASOUND

(75) Inventors: John I. Jackson, Menlo Park, CA (US); Constantine Simopoulos, San Francisco, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 896 days.

(21) Appl. No.: 11/643,270

(22) Filed: Dec. 21, 2006

(65) Prior Publication Data

US 2008/0154123 A1    Jun. 26, 2008

(51) Int. Cl.
*A61B 8/00* (2006.01)
(52) U.S. Cl.
USPC ........... 600/437; 600/424; 600/439; 600/443; 600/447; 600/466; 73/1.75; 73/1.79; 73/1.82; 73/1.86
(58) Field of Classification Search
USPC ... 600/424, 437, 439, 443, 447, 466; 73/1.75, 73/1.79, 1.82, 1.86
See application file for complete search history.

(56) References Cited

U.S. PATENT DOCUMENTS

| | | | | |
|---|---|---|---|---|
| 5,398,691 | A * | 3/1995 | Martin et al. | 600/463 |
| 5,787,889 | A * | 8/1998 | Edwards et al. | 600/443 |
| 6,122,538 | A * | 9/2000 | Sliwa et al. | 600/407 |
| 6,138,495 | A * | 10/2000 | Paltieli et al. | 73/1.86 |
| 6,311,540 | B1 * | 11/2001 | Paltieli et al. | 73/1.82 |
| 6,445,983 | B1 | 9/2002 | Dickson et al. | |
| 6,604,404 | B2 * | 8/2003 | Paltieli et al. | 73/1.82 |
| 6,607,488 | B1 * | 8/2003 | Jackson et al. | 600/443 |
| 6,708,055 | B2 * | 3/2004 | Geiser et al. | 600/425 |
| 6,716,166 | B2 * | 4/2004 | Govari | 600/437 |
| 6,773,402 | B2 * | 8/2004 | Govari et al. | 600/459 |
| 7,648,460 | B2 * | 1/2010 | Simopoulos et al. | 600/437 |
| 7,736,314 | B2 * | 6/2010 | Beach et al. | 600/437 |
| 2003/0153823 | A1 * | 8/2003 | Geiser et al. | 600/407 |
| 2004/0127793 | A1 * | 7/2004 | Mendlein et al. | 600/442 |
| 2005/0228280 | A1 * | 10/2005 | Ustuner et al. | 600/443 |
| 2005/0251013 | A1 * | 11/2005 | Krishnan et al. | 600/407 |
| 2006/0064017 | A1 * | 3/2006 | Krishnan et al. | 600/450 |

* cited by examiner

*Primary Examiner* — Tse Chen
*Assistant Examiner* — Baisakhi Roy

(57) ABSTRACT

Automated image interpretation is provided with transducer position and/or orientation sensing. The current position of a transducer is used to determine the anatomy being imaged. Other reference information, such as (1) the previous position of the transducer and the known anatomy being imaged at that time or (2) a reference device at a known location, is used in the determination. The anatomy is determined based on position sensing or determined based on position sensing and other anatomy features, such as image analysis.

4 Claims, 2 Drawing Sheets

AUTOMATED IMAGE INTERPRETATION WITH TRANSDUCER POSITION OR ORIENTATION SENSING FOR MEDICAL ULTRASOUND

BACKGROUND

The present embodiments relate to image interpretation. In particular, anatomical information associated with medical ultrasound images is determined.

Users of medical ultrasound imaging systems often manually annotate images with view information (e.g. "A2C" for cardiac applications, or "left kidney" for GI applications) or use graphical icons ("body markers"). The label may help with the later interpretation and diagnosis or analysis of the content of the image. Labeling also allows other automated processing programs to operate on the image with less required user actions. For example, an automated ejection fraction program asks the user to identify the clip as a cardiac apical 4-chamber (A4C) or apical 2-chamber (A2C) view, and then calculates the ejection fraction. However, manual labeling methods are time consuming and require high levels of concentration from the user, as well as skill and knowledge.

The label, such as the view, may be automatically determined. For example, a processor analyzes image content using feature recognition techniques or pattern recognition. Automated intelligent feature recognition and comparison with features in an image database identifies the view. However, pattern recognition may suffer from ambiguities introduced by the large number of patterns represented in the images with overlapping features.

As another example, the user may follow a protocol where the user first obtains a standard set of views in a standard, predefined order, such as done in cardiac stress echo exams. However, protocols do not allow deviation and may be unreliable.

Position sensors have been used on ultrasound transducers. The position sensors are used to determine the relative position between scan planes. A three-dimensional volume or extended field of view is scanned. A three-dimensional representation or extended field of view image is generated using the position information. Transesophageal transducers for imaging the heart have a mechanically determined rotation angle, which can be electronically controlled and displayed. The rotations may correspond to likely locations of different views of the heart.

BRIEF SUMMARY

By way of introduction, the preferred embodiments described below include a method, system, instructions, and computer readable media for automated image interpretation with transducer position and/or orientation sensing. The current position of a transducer is used to determine the anatomy being imaged. Other reference information, such as (1) the previous position of the transducer and the known anatomy being imaged at that time or (2) a reference device at a known location, is used in the determination. The anatomy is determined based on position sensing or determined based on position sensing and other anatomy features, such as image analysis.

In a first aspect, a method is provided for automated image interpretation with transducer position and/or orientation sensing. A position, orientation, or position and orientation of a transducer are sensed. A region of a patient is scanned with the transducer, and an image of the region is generated as a function of the scanning. Additional position information is acquired. The anatomy of the region represented in the image is determined as a function of the position, orientation, or position and orientation of the transducer and the additional position information.

In a second aspect, a system is provided for automated image interpretation with transducer position and/or orientation sensing. A transducer has a location device. An ultrasound imaging system is operable to scan an internal region of a patient with the transducer and generate an image of the region as a function of the scanning. The image represents anatomy of the region. A processor is operable to identify the anatomy of the region of the image as a function of position, orientation, or position and orientation of the transducer and additional position information.

In a third aspect, a computer readable storage medium has stored therein data representing instructions executable by a programmed processor for automated image interpretation with transducer position and/or orientation sensing. The storage medium includes instructions for determining transducer position, orientation, or position and orientation, and identifying anatomical structure represented by an ultrasound image as a function of the position, orientation, or position and orientation.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Knowledge of the anatomic view or content of an imaging region is useful for diagnosis, automated analysis, or cataloging of ultrasound images. Automatic labeling of anatomy may avoid or limit cumbersome, time consuming, and error prone manual entry or labeling. As an example of the workflow savings, if a cardiac clip is known to be an A4C or A2C view, then ejection fraction calculation, such as with AutoEF from Siemens Medical, can be run automatically and in the background.

A spatial or orientation transducer position sensor is used to determine or aid in determining the anatomic content of an ultrasound image data set. The view or position may be determined from location relative to a reference at a known location or from a previous position for a known view. The sensor may be used in combination with or without an image interpretation algorithm. The anatomical content, view, or position is then available for subsequent use, such as subsequent calculations or analysis.

Figure 1:
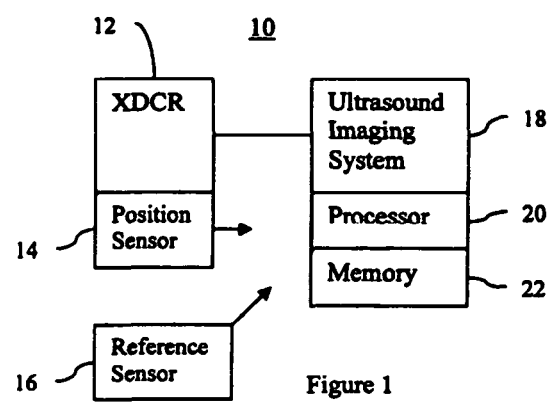
FIG. 1 is a block diagram of one embodiment of an ultrasound system for automated image interpretation with transducer position and/or orientation sensing.

FIG. 1 shows a system 10 for automated image interpretation with transducer position and/or orientation sensing. The system 10 includes a transducer 12, a location device 14, a reference sensor 16, an ultrasound imaging system 18, a processor 20, and a memory 22. Additional, different, or fewer components may be provided. For example, the system 10 does not include the reference device 14. As another example, the system 10 includes a display, and/or user interface. In one embodiment, the system 10 is a medical diagnostic ultrasound imaging system. In other embodiments, the processor 20 and/or memory 22 are part of a workstation or computer different or separate from the ultrasound imaging system 18. The workstation is adjacent to or remote from the ultrasound imaging system 18.

The transducer 12 is a single element transducer, a linear array, a curved linear array, a phased array, a 1.5 dimensional array, a two-dimensional array, a radial array, an annular array, a multidimensional array, or other now known or later developed array of elements. The elements are piezoelectric or capacitive materials or structures. In one embodiment, the transducer 12 is adapted for use external to the patient, such as including a hand held housing or a housing for mounting to an external structure. In other embodiments, the transducer 12 is adapted for use internal to the body, such as arrays mounted within catheters, transesophageal devices, or endocavity devices.

The transducer 12 converts between electrical signals and acoustic energy for scanning a region of the patient body. The region of the body scanned is a function of the type of transducer array and position of the transducer 12 relative to the patient. For example, a linear transducer array may scan a rectangular or square region of the body. As another example, a curved linear array may scan a pie shaped region of the body. Scans conforming to other geometrical regions or shapes within the body may be used, such as Vector® scans.

The transducer 12 includes the location device 14. The location device 14 is in or on the ultrasound transducer 12. For example, the location device 14 is mounted on, placed within, or formed as part of the housing of the transducer 12. In another example, the location device 14 is within an ultrasound imaging catheter. Signals or data are provided from or to the location device 14 with wires in the transducer cable or wirelessly.

The location device 14 is a sensor or sensed object. For example, the location device 14 includes coils of a magnetic position sensor. The coils sense a magnetic field generated by another device external to the sensor. Alternatively, the magnetic field is generated by the location device 14 and coils spaced from the location device 14 sense the position information of the transmitter.

The location device 14 may be part of a magnetic position sensor. Three orthogonal coils are provided. By sequencing transmission through remote transmitter coils and measuring signals on each of the sensors coils, the location and orientation of the sensor coil is determined. Based on the position and orientation of the patient relative to the transmitter coils, the location and orientation of the transducer 12 is determined. Precise position sensing, which may be required for volume acquisitions using position sensors, may not be required for determining anatomy. Alternatively, the location device 14 is a sensor for determining position for three-dimensional scanning.

Other location devices 14 may be used. For example, a gravity sensor that indicates the orientation of the transducer relative to the center of the earth is provided. In other examples, the location device 14 is an accelerometer or gyroscope.

Other orientation sensors may be used, for sensing one, two or three degrees of orientation relative to a reference. Other position sensors may be used with one, two or three degrees of position sensing. In other embodiments, a position and orientation sensor provide up to 6-degrees of position and orientation information. Examples of magnetic position sensors that offer the 6 degrees of position information are the Ascension Flock of Birds and the Biosense Webster position-sensing catheters.

The reference sensor 16 is also a location device. In one embodiment, the same type of location device as the location device 14 is used. Frequency, coding, timing or other characteristics allow separate position and/or orientation sensing of the reference sensor 16 and the location device 14. In other embodiments, the reference sensor 16 and the location device 14 are different types of devices.

The reference sensor 16 is a wireless or wired device for providing location information or receiving transmit information from the processor 20 or another device. The reference sensor 16 is positionable in a known location, such as over the sternum, at a left or right shoulder, or at the navel of the patient. Glue or other sticky material may maintain the reference sensor 16 in place.

The ultrasound imaging system 18 is a medical diagnostic ultrasound system. For example, the ultrasound imaging system 18 includes a transmit beamformer, a receive beamformer, a detector (e.g., B-mode and/or Doppler), a scan converter, and a display. The ultrasound imaging system 18 connects with the transducer 12, such as through a releasable connector. Transmit signals are generated and provided to the transducer 12. Responsive electrical signals are received from the transducer 12 and processed by the ultrasound imaging system 18. The ultrasound imaging system 18 causes a scan of an internal region of a patient with the transducer 12 and generates an image of the region as a function of the scanning. The image represents anatomy of the region, such as the heart, liver, fetus, muscle, tissue, fluid, or other anatomy.

In another embodiment, the ultrasound imaging system 18 is a workstation or computer for processing ultrasound data. Ultrasound data is acquired using an imaging system connected with the transducer 12 or using an integrated transducer 12 and imaging system. The data at any level of processing (e.g., radio frequency data (e.g., I/Q data), beamformed data, detected data, and/or scan converted data) is output or stored. For example, the data is output to a data archival system or output on a network to an adjacent or remote workstation. The ultrasound imaging system 18 processes the data further for analysis, diagnosis, and/or display.

The processor 20 is one or more general processors, digital signal processors, application specific integrated circuits, field programmable gate arrays, controllers, analog circuits, digital circuits, combinations thereof, network, or other logic devices for identifying anatomy of the region represented by an image. A single device is used, but parallel or sequential distributed processing may be used. In one embodiment, the processor 20 is a system controller of the ultrasound imaging system 18. The processor 20 receives inputs from the location device 14 and any reference sensor 16.

The processor 20 identifies the anatomy of the region of the image as a function of position information (e.g., position, orientation, or position and orientation) of the transducer and additional position information. The position, orientation, or position and orientation of the transducer 12 at a given time are provided using the location device 14. The information is an absolute or relative position. The position information and additional information are used to determine the content of the image. The anatomy is identified by approximation, assumption, or with any level of ambiguity. For example, having position information associated with less than 6 degrees of positioning or lower resolution of the position information may result in anatomic or scanning region ambiguity. However, the information may indicate likely anatomy or a short list of possible anatomies being scanned, identifying the anatomy.

Figure 2:
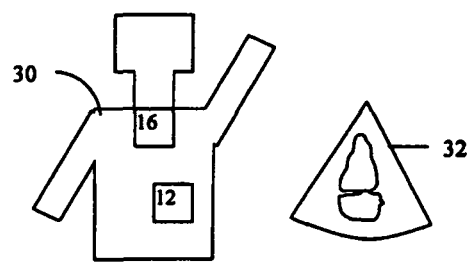
FIG. 2 is a graphical representation of a transducer relative to a patient and the corresponding image of anatomy within the patient.

In one embodiment, the processor 20 determines the anatomy using a reference position relative to a known location on the patient. FIG. 2 shows a patient 30 with the transducer 12 on the abdomen and the reference sensor 16 located on the sternum. The reference sensor 16 may be located elsewhere. The location of the reference sensor 16 on the patient is predetermined or may be entered by the user. The relative position information of the transducer 12 to the reference sensor 16 indicates a location of the transducer 12 on the patient. A model, such as a table of relative positions and corresponding anatomy, is used to relate the relative position to the anatomy being scanned. The model used may depend on the location of the reference sensor 16. Other models may be used, such as a database of relative positions and corresponding anatomy corresponding to a number of patients. The determined anatomic view and anatomy would be derived, at least in part, by the positions and anatomies in the database that most closely match, in some sense, the relative position of the currently-being-acquired image.

In another embodiment, the user positions the transducer 12 at one or more predetermined locations on the patient. The position of the transducer 12 when placed at each predetermined location is stored. The relative position of the transducer 12 during use to at least one predetermined location is used to determine the anatomy. For example, the position process noted in U.S. Pat. No. 6,607,488, the disclosure of which is incorporated herein by reference, is used. As an alternative, the previous position of the transducer 12 associated with known anatomy, view, or location relative to the patient is used without predetermined location. For example, the user positions the transducer 12 to scan one heart view. User entry, protocol, image processing, or other analysis identifies this one heart view. As the transducer is moved, subsequent anatomy may be identified by the relative position with the previous position and a model associating the known information to the relative position. Other sources of additional information to indicate anatomy relative to a current position may be used.

The anatomy information is provided to the user, such as on a display, stored with the image, or both. By labeling the image with the anatomy or position information indicating the anatomy, the image may be later identified as related to that anatomy. For example, a database of images is provided, with each image labeled. The database is searched with an anatomy parameter to identify the image or groups of images for the anatomy.

The anatomy may be used for other purposes. The processor 20 or other device performs a calculation as a function of the anatomy. For example, ejection fraction is automatically calculated once images representing a desired number of different heart views are obtained. By automatically determining the anatomy, the calculation may be performed without user initiation after generating the image. The calculation routine runs in the background rather than requiring user initiation after imaging.

The processor 20 or another device may apply a computer assisted diagnosis algorithm to the image. The computer assisted diagnosis algorithm is selected, configured, or selected and configured as a function of the anatomy. For example, different computer assisted diagnosis algorithms may be trained or optimized for different anatomy. The anatomy being imaged is identified and used to select the appropriate algorithm.

In another embodiment, the processor 20 applies an image interpretation algorithm. The image interpretation algorithm uses information derived from the image, such as features identified from image data, to indicate anatomy. In addition to the image-based information, the position, orientation, or position and orientation of the transducer may be used to identify the anatomy. In one embodiment, the position information is a variable, such as an image feature, in the image interpretation algorithm. The variables are processed to identify the anatomy represented in the image.

The memory 22 is a tape, magnetic, optical, hard drive, RAM, buffer or other memory. The memory 22 stores the image and a label of the anatomy corresponding to the image. The label may be text describing the anatomy. The label may be position information on the patient, indicating the anatomy. The label may be an annotation entry on the image. Other labeling may be used.

The memory 14 is additionally or alternatively a computer readable storage medium with processing instructions. Data representing instructions executable by the programmed processor 20 identify anatomy. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

In one embodiment, the computer readable storage medium has stored therein data representing instructions executable by the programmed processor 20 for automated image interpretation with transducer position and/or orientation sensing. The instructions are for determining transducer position, orientation, or position and orientation. Anatomical structure represented by an ultrasound image is identified as a function of the position, orientation, or position and orientation. For example, the instructions include an automatic view identification algorithm for identifying the anatomical structure. The position, orientation, or position and orientation are variables of the automatic view identification algorithm. The automatic view identification algorithm also determines the structure based, at least in part, on image data. The instructions may also include other acts discussed herein, such as calculating a parameter associated with the anatomical structure in response to identification of the anatomical structure.

Figure 3:
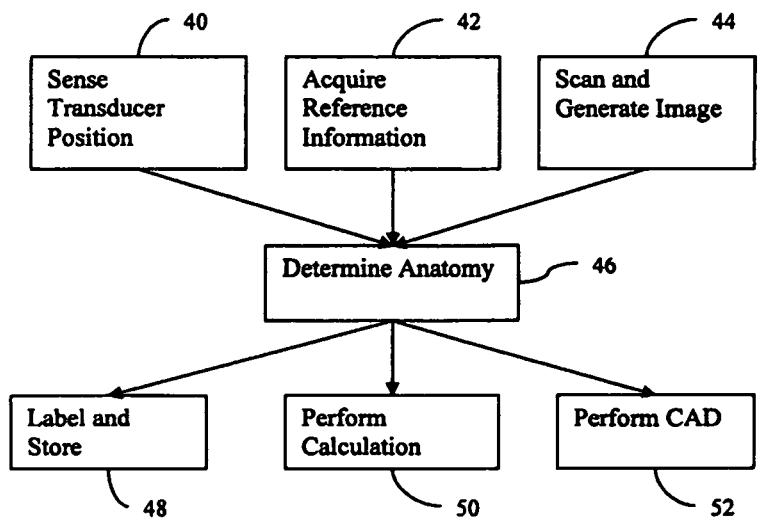
FIG. 3 is a flow chart diagram of one embodiment of a method for automated image interpretation with transducer position and/or orientation sensing.

FIG. 3 shows a method for automated image interpretation with transducer position and/or orientation sensing. The acts shown in FIG. 3 are performed in the order shown or a different order. Additional, different, or fewer acts may be performed. For example, acts 48, 50, and 52 are optional.

In act 40, position information of a transducer is sensed. The position information is a position, orientation, or position and orientation of the transducer. The position information corresponds to one or more degrees of freedom or sensing, such as sensing 6 degrees of freedom (three translational axes and three rotational axes). The position information is sensed at the transducer or based on signals sent from the transducer. In one embodiment, a magnetic position sensor connected with the transducer senses the position information. In other embodiments, a gravity sensor, accelerometer, gyroscope, optical pattern recognition, infrared, radio frequency, or other position sensing is used.

In act 42, additional position information is acquired. The additional position information relates the transducer position to the patient. For example, a position of a reference device is determined. The reference device is located at a known position on the patient. The relative position of the transducer to the reference device and the known position of the reference device indicate the position of the transducer on and/or scan region within the patient. The relative position to the reference device is determined at a same or similar time as the position information of act 40, such as acquiring the position information of act 40 as the relative position to the reference device (e.g., the reference device being a transmitter or sensor and the transducer being associated with the other of the sensor or transmitter).

As another example, a previous position of the transducer at a known anatomical location or associated with a known view is acquired. Changes from the previous position are associated with anatomy based on the known view at the previous position.

In act 44, a region of a patient is scanned with the transducer. Any ultrasound scan format may be used, such as a linear, sector, or Vector®. A single range gate, a scan line, a two-dimensional region, or a volume is scanned. Using beamforming or other processes, data representing the scanned region is acquired. Also in act 44, an image of the region is generated as a function of the scanning. For example, a two-dimensional image is generated by detection and scan conversion of the beamformed information. A single image is generated. FIG. 2 shows an example image 32 of an A2C view of the anatomy of the heart. Alternatively, a sequence of images representing the same or different regions are obtained.

In act 46, the anatomy of the region represented in the image is determined. The anatomy is determined as a function of the position, orientation, or position and orientation of the transducer and the additional position information from acts 40 and 42.

In one embodiment of act 46, the anatomy is determined from the position, orientation, or position and orientation of the transducer relative to a reference position and a model of relative locations of anatomy within the patient. The transducer is placed in a location and with an orientation to a reference sensor. Based on the relative position, a best guess is made of the anatomical view. Subsequent movements of the transducer are recorded relative to the reference, so transducer rotation and/or translation can be compared with those expected for standard imaging views in the model. Motion or positioning outside of a standard range for each view may be labeled as "unknown view," a most likely view is selected, or a list of possible views are output. Alternatively, the relative position and scan plane depth/width are used to identify anatomy, such as an organ. The anatomy is listed as the organ or organs likely intersected by the scan plane.

In another embodiment of act 46, the anatomy is determined from the position, orientation, or position and orientation of the transducer relative to a previous position and a model of relative locations of the anatomy with the known anatomical location or view. For example, an A4C view of heart anatomy is imaged and identified. The change in position of the transducer associated with an about 90-110 degrees rotation is detected. The model indicates rotation of 80-120 degrees or other range of values from the A4C view as being an A2C view, identifying the anatomy.

The anatomy is determined only from the position information and the additional position information. Alternatively, additional information is used. For example, the anatomy of the region is determined with an image interpretation algorithm. The position, orientation, position and orientation of the transducer, the additional position information, and information derived from image data are variables used by the image interpretation algorithm to determine anatomy. Feature analysis of the image is used in combination with the position to further increase confidence in the image labeling.

To improve the robustness of image interpretation, additional information provided by a position/orientation sensor in the housing of a medical ultrasound transducer is input. Image recognition software is utilized to identify and/or interpret an ultrasound image. Image interpretation helps optimize the operating parameters of an ultrasound system or initiate a measurement of clinical parameters.

Typically, cardiology exams are performed in a standard position of the patient. A complete exam covers various standard views, which are accessed from different positions and orientations of the transducer with respect to the patient's body. If these orientations are known using a gyroscope, an accelerometer, or other device, then that information can help discriminate between two views that otherwise might have been ambiguous by using machine vision and pattern recognition techniques alone.

Introducing position information allows identifying groups of images unambiguously or less ambiguously, reducing the number of different images that the vision based algorithm has to discriminate or assisting in discriminating. For example, in cardiology, 13 or other number of different standard views of the heart exist. A vision-based algorithm needs to discriminate between them accurately. With data from the position/orientation sensor, the imaging window may be identified, such as whether the view is parasternal or apical. In this case, the machine vision based algorithm then discriminates between 5 different views at most. Even if the orientation of the transducer is not known with respect to the patient's body, the knowledge of the spatial relationship of images acquired during the exam adds enough discriminating power, allowing the grouping of the images according to their orientation. This would be the case for instance with fetal hearts where the position of the fetus with respect to the transducer is difficult to control. In another example, the image features and position information are used together to discriminate between two views instead of or in addition to the hierarchal approach. Alternatively, the position information is used to verify computer based image interpretation.

The fusion of other information may be used. For example, inputs from other types of sensors may assist in anatomy identification. A standard protocol provides for acquiring view A first, followed by view B, and then usually by view C. The most common ordering is used as input to determine anatomy. Different anatomy determinations may be used in combination to further increase confidence in the image labeling, such as both feature analysis and use of a protocol in combination with the position sensor.

In act 48, the image is labeled. An indication of the anatomy is annotated onto or provided with the image. Alternatively or additionally, the image and the label are stored. Views are accordingly labeled on the screen and stored with the image data. Automatic labeling of images may permit sorting and standardized presentation order for a series of acquired images. In addition to saving the view, the absolute or relative physical location of the transducer associated with each acquired image may be presented and/or stored. Displayed position information indicates the relative angle or position of an image relative to a previous image. For example, after acquiring an apical four-chamber (A4C) cardiac view, the user may move to an apical two-chamber (A2C) view, by maintaining the transducer center position but rotating the transducer by, for example, 105 degrees. Either or both of the new view label (A2C) or the relative or absolute position or orientation (105 degrees) may be displayed, saved with the associated images, or be used in subsequent analysis.

The label may be verified. For example, the user may override a displayed label. As another example, the label may not be stored with the image unless a user actively confirms correct labeling.

In act 50, a calculation is performed as a function of the anatomy. For example, multiple apical cardiac views, each with a different but measured and known rotation angle, are combined to determine estimated left ventricular chamber volume and ejection fraction. The anatomy information indicates which images to combine for best representing the heart.

The calculation is performed in response to user activation. Alternatively, the calculation is performed without user initiation after generating the image. The identification of the anatomy triggers calculation.

In one embodiment, the anatomy at the location of a Doppler gate is determined. The anatomy may facilitate automatic analysis of the spectral Doppler data and/or image. Spectral Doppler analysis can be tuned and different measurements made for each heart valve and flow state. Determining the heart valve in an image or associated with the Doppler gate, allows automated tuning or selection of measurements.

In act 52, a computer assisted diagnosis algorithm is applied to the image. The computer assisted diagnosis algorithm is selected, configured, or selected and configured as a function of the anatomy. After identifying the anatomy, automated analysis may be performed. The analysis is optimized for the anatomy.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for automated image interpretation with transducer position and/or orientation sensing, the method comprising:

sensing a position, orientation, or position and orientation of a transducer;

scanning a region of biological tissue within a patient with the transducer;

generating an image of the region as a function of the scanning;

acquiring additional position information as a reference position to a known location on the patient;

determining, with a processor, an identification of anatomy of the region represented in the image as a function of the position, orientation, or position and orientation of the transducer relative to the additional position information, the reference position and a model of relative locations of anatomy within the patient; and determining a label of the anatomy from the identification.

2. A method for automated image interpretation with transducer position and/or orientation sensing, the method comprising:

sensing a position, orientation, or position and orientation of a transducer;

scanning a region of biological tissue within a patient with the transducer;

generating an image of the region as a function of the scanning;

acquiring additional position information as a reference to a known location on the patient and a previous position of the transducer, the previous position corresponding to a known anatomical location or view;

determining, with a processor, an identification of anatomy of the region represented in the image as a function of the position, orientation, or position and orientation of the transducer relative to the additional position information, the previous position and a model of relative locations of the anatomy with the known anatomical location or view; and determining a label of the anatomy from the identification.

3. A system for automated image interpretation with transducer position and/or orientation sensing, the system comprising:

a transducer having a location device;

an ultrasound imaging system operable to scan an internal region of a patient with the transducer and generate an image of the region as a function of the scanning, the image representing anatomy of the region; and a processor configured to identify the anatomy of the region of the image as a function of position, orientation, or position and orientation of the transducer relative to additional position information as a reference to a known location on the patient, the processor configured to determine a label of the anatomy from the identity, and wherein the additional position information comprises a reference position relative to the known location on the patient, and wherein the processor is configured to identify the anatomy from the position, orientation, or position and orientation of the transducer relative to the reference position and a model of relative locations of anatomy within the patient.

4. A system for automated image interpretation with transducer position and/or orientation sensing, the system comprising:

a transducer having a location device;

an ultrasound imaging system operable to scan an internal region of a patient with the transducer and generate an image of the region as a function of the scanning, the image representing anatomy of the region;

a processor configured to identify the anatomy of the region of the image as a function of position, orientation, or position and orientation of the transducer relative to additional position information as a reference to a known location on the patient, the processor configured to determine a label of the anatomy from the identity and;

wherein the additional position information comprises a previous position of the transducer, the previous position corresponding to the known location comprising a known anatomical location or view, and wherein the processor is configured to identify the anatomy from the position, orientation, or position and orientation of the transducer relative to the previous position and a model of relative locations of the anatomy with the known anatomical location or view.

\* \* \* \* \*